United States Patent
Arata et al.

(10) Patent No.: US 10,028,880 B2
(45) Date of Patent: Jul. 24, 2018

(54) HAND EXOSKELETON DEVICE

(71) Applicant: KYUSYU UNIVERSITY, NATIONAL UNIVERSITY CORPORATION, Fukuoka (JP)

(72) Inventors: Jumpei Arata, Fukuoka (JP); Roger Gassert, Zurich (CH)

(73) Assignee: Kyushu University, National University Corporation, Fukuoka-shi, Fukuoka (JP)

(*) Notice: Subject to any disclaimer, the term of this patent is extended or adjusted under 35 U.S.C. 154(b) by 527 days.

(21) Appl. No.: 14/773,075

(22) PCT Filed: Mar. 7, 2014

(86) PCT No.: PCT/JP2014/056032
§ 371 (c)(1),
(2) Date: Sep. 4, 2015

(87) PCT Pub. No.: WO2014/136958
PCT Pub. Date: Sep. 12, 2014

(65) Prior Publication Data
US 2016/0015590 A1    Jan. 21, 2016

(30) Foreign Application Priority Data
Mar. 8, 2013  (JP) .................... 2013-046449

(51) Int. Cl.
*A61F 2/78* (2006.01)
*A61H 1/02* (2006.01)
(Continued)

(52) U.S. Cl.
CPC ........... *A61H 1/0288* (2013.01); *A61F 2/583* (2013.01); *A61F 2/586* (2013.01); *A61F 2/78* (2013.01);
(Continued)

(58) Field of Classification Search
None
See application file for complete search history.

(56) References Cited

U.S. PATENT DOCUMENTS 2,885,686 A * 5/1959 Giaimo ............... A61F 2/72
 116/205
4,167,044 A * 9/1979 Girard ................. A61F 2/72
 602/20

(Continued)

FOREIGN PATENT DOCUMENTS

EP  2417941 A1  2/2012
JP  50-28551 Y1  8/1975
(Continued)

OTHER PUBLICATIONS

Extended European Search Report dated Oct. 14, 2016, by the European Patent Office in counterpart European Application No. 14761013.3.
(Continued)

*Primary Examiner* — Stephen R Crow
(74) *Attorney, Agent, or Firm* — Sughrue Mion, PLLC

(57) ABSTRACT

In a hand exoskeleton device, according to a three-layered sliding spring mechanism, the motion of the device is changed by a single drive mechanism to transmit power to the metacarpophalangeal, proximal and distal interphalangeal joints of a human finger, thereby enabling support of the daily activity motions of the finger. According to the hand exoskeleton device, when compared with a conventional device, there can be realized a device which is small in size and weight and is capable of supporting the gripping motions of the human finger. The hand exoskeleton device is characterized in that the three joints of the finger can be bent and extended by the single drive mechanism and it can transmit large drive power. Further, the device body is flexible, thereby enabling safe movement.

7 Claims, 3 Drawing Sheets

(51) Int. Cl.
  *B25J 9/00* (2006.01)
  *A61F 2/58* (2006.01)
(52) U.S. Cl.
  CPC ..... *B25J 9/0006* (2013.01); *A61F 2002/7862* (2013.01); *A61H 2201/149* (2013.01); *A61H 2201/1481* (2013.01); *A61H 2201/165* (2013.01); *A61H 2201/1635* (2013.01); *A61H 2201/1664* (2013.01); *A61H 2201/1676* (2013.01); *A61H 2201/5007* (2013.01); *A61H 2230/605* (2013.01)

(56) References Cited

U.S. PATENT DOCUMENTS

| | | | | |
|---|---|---|---|---|
| 4,834,761 | A * | 5/1989 | Walters | B25J 9/104 254/228 |
| 5,807,376 | A * | 9/1998 | Viola | A61B 17/00234 414/1 |
| 8,998,831 | B2 | 4/2015 | Sankai | |
| 2010/0249676 | A1 | 9/2010 | Kawakami | |
| 2012/0029399 | A1 | 2/2012 | Sankai | |

FOREIGN PATENT DOCUMENTS

| | | |
|---|---|---|
| JP | 62188381 U | 11/1987 |
| JP | 200559110 A | 3/2005 |
| JP | 2010-63723 A | 3/2010 |
| JP | 2013-240464 A | 12/2013 |
| WO | 2013/012029 A1 | 1/2013 |

OTHER PUBLICATIONS

Search Report dated Apr. 15, 2014, issued by the International Searching Authority in counterpart International Application No. PCT/JP2014/056032.

Shields et al.; "An Anthropomorphic Hand Exoskeleton to Prevent Astronaut Hand Fatigue During Extravehicular Activities", IEEE Transactions on Systems, MAN, and Cybernetics—Part A: Systems and Humans, vol. 27, No. 5, Sep. 1997, p. 668-673.

Satoshi Ito et al.; "A design of fine motion assist equipment for disabled hand in robotic rehabilitation system", Journal of the Franklin Institute, 348 (2011), p. 79-89.

T.T. Worsnopp et al.; "An Actuated Finger Exoskeleton for Hand Rehabilitation Following Stroke", IEEE 10th International Conference on Rehabilitation Robotics, Jun. 12-15, 2007, p. 896-901.

Hasegawa et al.; "Five-Fingered Assistive Hand with Mechanical Compliance of Human Finger", 2008 IEEE International Conference on Robotics and Automation, May 19-23, 2008, p. 718-724.

Connelly et al.; "A Pneumatic Glove and Immersive Virtual Reality Environment for Hand Rehabilitative Training after Stroke", 2010 IEEE, Total 10 pages.

Tadano et al.; "Development of Grip Amplified Glove with Exoskeletal Structure using Pneumatic Artificial Rubber Muscle", The Japan Society of Mechanical Engineers, [No. 09-4] Proceedings of the 2009 JSME Conference on Robotics and Mechatronics, May 24-26, 2009, Total 4 pages.

Arata et al.; "A hand exoskeleton robot for rehabilitation using a three-layered sliding spring mechanism", The Japan Society of Mechanical Engineers, No. 12-3 Proceedings of the 2012 JSME Conference on Robotics and Mechatronics, May 27-29, 2012, Total 3 pages.

Arata et al.; "A new hand exoskeleton device for rehabilitation using a three-layered sliding spring mechanism", 2013 IEEE International Conference on Robotics and Automation (ICRA), p. 3902-3907.

Communication issued by the Japanese Patent Office dated Sep. 19, 2017 in counterpart Japanese Patent Application No. 2015-504425.

Jumpei Arata et al., "A hand exoskeleton robot for rehabilitation using a three-layered sliding spring mechanism", Proceeding of the 2012 JSME Conference on Robotics and Mechatronics, May 27-29, 2012, pp. 2-4, No. 12-3, Hamamatsu, Japan.

Office Action dated May 8, 2018 by the Japanese Patent Office in counterpart Japanese Patent Application No. 2015-504425.

* cited by examiner

HAND EXOSKELETON DEVICE

TECHNICAL FIELD

The present invention relates to a hand exoskeleton device. For example, the present invention relates to a hand exoskeleton device using a three-layered sliding spring mechanism which is mounted on a human body for supporting finger motions. Also, for example, the present invention relates to a hand exoskeleton device using a three-layered sliding spring mechanism for supporting finger flexion and extension movements.

BACKGROUND ART

Medical rehabilitation on physical function is performed in a hospital or the like in order to recover physical function lowered by disease or injury. Recently, for a more effective function recovery method, quantitative evaluation of function recovery, reduction of burden of rehabilitation workers or the like, there have been made attempts to apply robot technology to rehabilitation. Especially, attempts to mount a robot or the like for supporting lowered physical function and daily living activity have been made actively.

As a conventional hand exoskeleton device using a link mechanism, there are known Non-Patent Literature 1, Non-Patent Literature 2 and the like. As a device using a wire mechanism, there are known Non-Patent Literature 3, Non-Patent Literature 4 and the like. As a device using fluid drive, there are known Non-Patent Literature 5, Non-Patent Literature 6 and the like. Also, Non-Patent Literature 7 provides a mechanism using a three-layered connecting sliding spring.

CITATION LIST

Non-Patent Literature

Non-patent Literature 1: B. L. Shields, J. A. Main, S. W. Peterson, A. M. Strauss, "An Anthropomorphic Hand Exoskeleton to Prevent Astronaut Hand Fatigue During Extravehicular Activities," IEEE Transactions on Systems, Man, and Cybernetics Part A: Systems and Humans, 27(5), 1997.

Non-patent Literature 2: S. Ito, H. Kawasaki, Y. Ishigure, M. Natsume, T. Mouri, Y. Nishimoto, "A design of fine motion assist equipment for disabled hand in robotic rehabilitation system," Journal of the Franklin Institute, 2009.

Non-patent Literature 3: T. T. Worsnopp, M. A. Peshkin, J. E. Colgate, and D. G. Kamper, "An Actuated Finger Exoskeleton for Hand Rehabilitation Following Stroke," IEEE10th International Conference on Rehabilitation Robotics, pp. 896-901, 2007.

Non-patent Literature 4: Y. Hasegawa, Y. Mikami, K. Watanabe, Y. Sankai, "Five-Fingered Assistive Hand with Mechanical Compliance of Human Finger," 2008 IEEE International Conference on Robotics and Automation, pp. 718-724, 2008.

Non-patent Literature 5: L. Connelly, Y. Jia, M. L. Toro, M. E. Stoykov, R. V. Kenyon, D. G. Kamper, "A Pneumatic Glove and Immersive Virtual Reality Environment for Hand Rehabilitative Training After Stroke," IEEE Transactions on Neutral Systems and Rehabilitation Engineering, 18(5), pp. 551-559, 2010.

Non-patent Literature 6: Koutaro Tadano, Masao Akai, Kazuo Kadota, Kenji Kawashima, "Development of Exoskeleton Type Grip Amplification Glove using Pneumatic Artificial Muscle", Lecture on Robotics and Mechatronics, 1P1-E15, 2009.

Non-patent Literature 7: Junpei Arata, Keiichi Ohmoto, Roger Gassert, Oliver Lambercy, Hideo Fujimoto, Ikuo Wada, "Development of Hand Exoskeleton device prototype using three-layered Connecting Sliding spring Mechanism," Instrument Automatic Control Society, System Integration Department, Lecture Proceedings, pp. 2458-2459, 2012.

SUMMARY OF INVENTION

Technical Problem

Requirements of a device for supporting finger daily activity motions include, for example: it is small in size and light in weight; it is mountable on a human body and is capable of natural motion; it can generate sufficient power for supporting the motions; and, it can be driven safely.

A drive mechanism constituting such device, conventionally, includes a link drive mechanism, a wire drive mechanism and a fluid drive mechanism.

The link drive mechanism is used to transmit finger motions to the tip end thereof through a link to thereby drive the respective finger joints. The link drive mechanism can easily achieve a relatively large output but the device is likely increased in size. Also, the link drive part has often mechanical play.

The wire drive mechanism is used to drive joints using a wire. Since a transmission route is reduced in size and in diameter using the wire, the whole mechanism can be made small-sized. Meanwhile, since the wire is capable of power transmission only in the tensile force direction, the power part mechanism tends to be complicated. Also, the wire extends and shrinks.

The fluid drive mechanism provides a technique to fill fluid into the mechanism and generate drive power using variations in the pressure thereof. With this mechanism, a device to wear on a human body can be worn compact, meanwhile it needs an actuator for compressing the fluid.

A conventionally developed mechanism using a three-layered connecting sliding spring, when compared with the link drive mechanism, wire drive mechanism and fluid drive mechanism, is advantageous in that it is small in size and light in weight. However, since it includes multiple movable parts therein, it is complicated in structure.

The present invention is made in view of the above circumstances and an object of the present invention is to provide a hand exoskeleton device having a new structure for supporting human finger motions.

Solution to Problem

In order to achieve the above-mentioned object, an aspect of the present invention provides a hand exoskeleton device being a three-layered sliding spring mechanism drivable by a drive mechanism and mountable on a finger, the hand exoskeleton device including: a zeroth outer mounting part, a first outer mounting part, a second outer mounting part and a third outer mounting part arranged in series along a longitudinal direction of the finger from a tip end of the hand exoskeleton device, wherein the zeroth outer mounting part and the first mounting part, the first outer mounting part and the second mounting part, and the second outer mounting part and the third outer mounting part are respectively connected to each other by multiple sets of upper springs and lower springs arranged in parallel in a vertical direction, the upper springs for fixing upper portions of the respective outer mounting parts are variable in length so that fixed ends of the upper springs are freely movable with sliding mechanisms by a specific distance in the finger longitudinal direction, the lower springs for fixing lower portions of the respective outer mounting parts are fixed at both ends to the respective outer mounting parts, the respective outer mounting parts include therein a drive spring capable of freely sliding only in the finger longitudinal direction, a tip end of the drive spring is fixed to the zeroth outer mounting part and the other end of the drive spring is fixed to a drive shaft, and the upper and lower springs connecting together the outer mounting parts and the drive spring constitute three layers in the vertical direction, wherein where the hand exoskeleton device is mounted onto a finger of a human body, the zeroth outer mounting part is fixed to a portion ranging from a distal interphalangeal joint to a terminal end of the finger, the first outer mounting part is fixed to a portion intervening between the distal interphalangeal joint and a proximal interphalangeal joint of the finger, the second outer mounting part is fixed to a portion intervening between the proximal interphalangeal joint and metacarpophalangeal joint of the finger, and the third outer mounting part is fixed to a palm part of the human body, and while the hand exoskeleton device is mounted on the human body, the drive shaft is driven on the finger of the human body in the longitudinal direction of the finger of the human body, thereby applying torque to the distal interphalangeal joint, the proximal interphalangeal joint and the metacarpophalangeal joint of the finger to support flexion and extension movements of the finger of the human body.

According to an aspect of the present invention, in the three-layered sliding spring mechanism, lengths of the upper and lower springs respectively connecting together the zeroth outer mounting part, the first outer mounting part, the second outer mounting part and the third outer mounting part and a length of the drive spring serve as indexes for changing a timing for flexing the respective joints, and motions are adjustable by changing the spring length.

The aspect of the present invention provides a hand exoskeleton device to be mounted on the human body for supporting the finger motions, in which, using the three-layer sliding spring mechanism, torque is supplied by the single drive mechanism simultaneously to the distal interphalangeal joint (DIP joint), proximal interphalangeal joint (PIP joint) and intermediate interphalangeal joint (MP joint) of a finger, and the device main body operates to follow the natural motions of the human body.

The device is disposed on the nail side constituting the upper part of the human finger so as to follow the finger. Thus, a direction going from the device to the finger side is called a lower direction, whereas the opposite direction is called an upper direction.

The three-layered sliding spring mechanism according to the aspect of the present invention includes a zeroth outer mounting part, a first outer mounting part, a second outer mounting part and a third outer mounting part arranged in series from the tip end thereof along the finger longitudinal direction.

The zeroth and first outer mounting parts, the first and second outer mounting parts, and the second and third outer mounting parts are respectively connected together in the vertical direction by their respective spring elements. The lower springs for fixing the lower portions of the outer mounting parts are fixed at both ends to the respective outer mounting parts.

Since the upper springs for fixing the upper portions of the outer mounting parts are capable of moving their fixed ends freely by the slider mechanisms in the finger longitudinal direction, their lengths are variable.

The lower springs for fixing the lower portions of the outer mounting parts are fixed to the both ends of the respective lower portions.

The outer mounting parts respectively incorporate therein a drive spring capable of freely sliding only in the finger longitudinal direction, while the tip ends of the drive spring are fixed to the zeroth outer mounting part and the other ends thereof are fixed to the drive shaft.

Thus, the upper springs for connecting together the outer mounting parts, lower springs for connecting together the outer mounting parts and drive spring constitute three layers in the vertical direction.

The respective outer mounting parts are fixed to the respective portions of a finger serving as a mounting target using a flexible belt or the like. In this case, the zeroth outer mounting part is fixed to the portion ranging from the DIP joint to the terminal end, the first outer mounting part is fixed to the portion intervening between the DIP joint and PIP joint, and the second outer mounting part is fixed to the portion intervening between the PIP joint and MP joint, and the third outer mounting part is fixed to the palm portion, respectively.

The zeroth, first, second, third mounting parts and drive shaft are respectively formed of material having a sufficient strength to the springs connecting them together.

According to this structure, the present invention can be applied as a device which, when mounted on a human body, by driving the drive shaft in the longitudinal direction relative to a human finger, applies torque to the DIP joint, PIP joint and MP joint to support the natural gripping motions of the finger.

DESCRIPTION OF EMBODIMENTS

The hand exoskeleton device according to an embodiment of the present invention can be easily mounted onto a human body, and can operate a three-layered sliding spring mechanism serving as a motion transfer mechanism for applying drive power to a distal interphalangeal joint (DIP joint), a proximal interphalangeal joint (PIP joint) and a metacarpophalangeal joint (MP joint) using a single direct acting actuator, thereby supporting the gripping motions of the human body with the device mounted thereon.

Description is given below specifically of an example of a preferred embodiment of the present invention with reference to the drawings.

Figure 1:
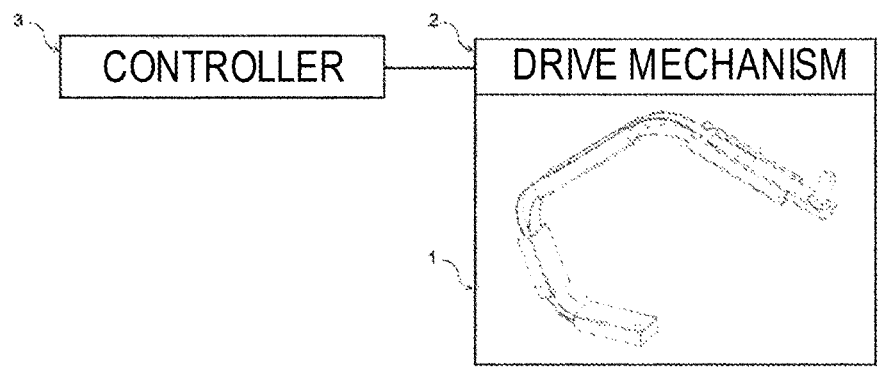
FIG. 1 is a diagram of a hand exoskeleton device system using a three-layered sliding spring mechanism according to an embodiment of the present invention.

FIG. 1 shows a hand exoskeleton device system using a three-layered sliding spring mechanism according to the embodiment of the present invention.

The hand exoskeleton device system according to the embodiment of the present invention includes a three-layered sliding spring mechanism 1, and a controller 3 for controlling a drive mechanism 2 of the three-layered sliding spring mechanism 1. This system is mounted on a finger part of a human body and is used to support the motions of the finger part. Also, it is used for passive repetitive motions in rehabilitation.

Figure 2:
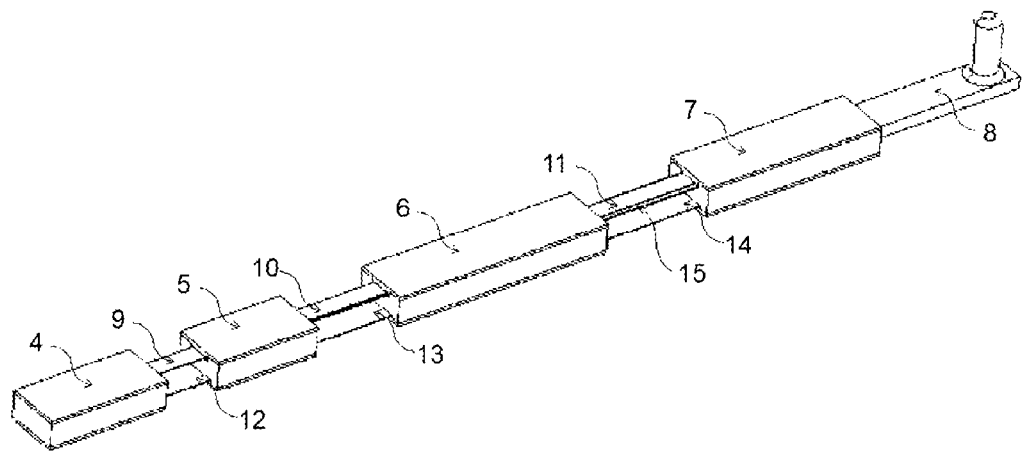
FIG. 2 is a perspective view of a three-layered sliding spring mechanism model according to an embodiment of the present invention.
Figure 3:
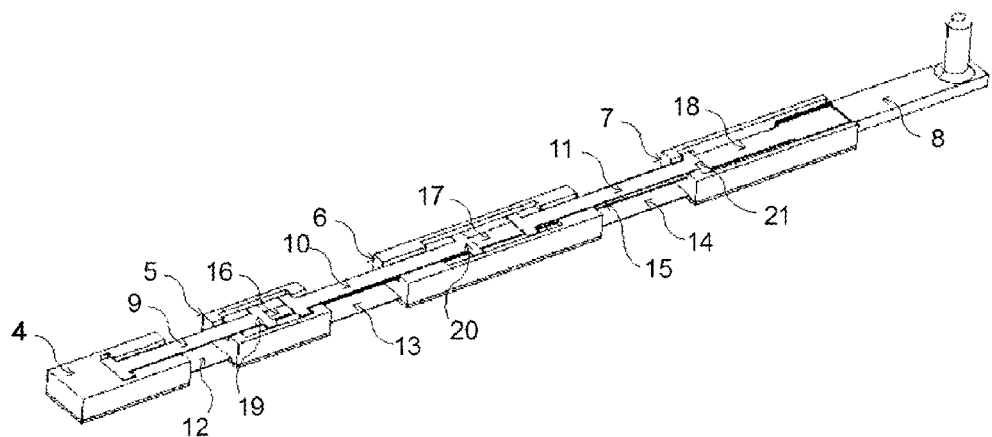
FIG. 3 is a partially transparent perspective view of the three-layered sliding spring mechanism model according to the embodiment of the present invention.
Figure 4:
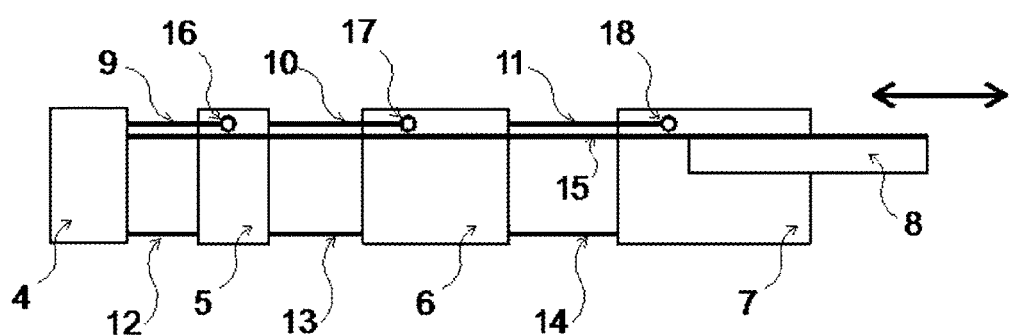
FIG. 4 is a conceptual diagram of the structure of the three-layered sliding spring mechanism according to the embodiment of the present invention.

Next, referring to FIGS. 2 to 4, description is given specifically of the structure of three-layered sliding spring mechanism 1. FIG. 2 is a perspective view of a mechanism model of the embodiment, FIG. 3 is a transparent perspective view of outer mounting parts constituting part of the mechanism model of the embodiment, and FIG. 4 is a conceptual diagram of the structure of the mechanism of the embodiment.

The three-layered sliding spring mechanism 1 includes a zeroth outer mounting part 4, a first mounting part 5, a second outer mounting part 6, a third mounting part 7, and a drive shaft 8. The respective outer mounting parts 4 to 7 are connected in series by springs 9 to 15 respectively formed of plate springs.

The first outer mounting upper spring 9, second outer mounting upper spring 10 and third outer mounting upper spring 11 connect the upper portions of the outer mounting parts 4 to 7 and are allowed to slide freely in the longitudinal direction of the sliding spring mechanism 1, that is, in the mechanism longitudinal direction by a first slider mechanism 16, a second slider mechanism 17 and a third slider mechanism 18, respectively. Thus, the first, second and third outer mounting upper springs 9, 10 and 11 are respectively flexible springs having variable lengths. However, the sliding distances of the respective springs 9, 10 and 11 with respect to their respective outer mounting parts 4 to 7 can be limited by stoppers 19, 20 and 21 respectively provided within the slider mechanisms 16, 17 and 18.

A first outer mounting lower spring 12, a second outer mounting lower spring 13 and a third outer mounting lower spring 14 connect the lower portions of the outer mounting parts 4 to 7 respectively. The lower springs 12, 13 and 14 are respectively fixed to the outer mounting parts 4 to 7 which are to be connected to the respective two ends of the springs.

The drive spring 15 is inserted such that it is freely slidable only in the finger longitudinal direction within the respective outer mounting parts 4 to 7, while the tip end of the drive spring 15 is fixed to the zeroth outer mounting part 4 with the other end fixed to the drive shaft 8.

In this case, the outer mounting (parts) upper springs 9 to 11, the outer mounting (parts) lower springs 12 to 14 and drive spring 15 respectively constitute three layers in the mechanism vertical direction. And, the drive spring 15 is interposed between the outer mounting parts upper springs 9 to 11 and the outer mounting parts lower springs 12 to 14 in the mechanism vertical direction.

When the device being the sliding spring mechanism 1 is fixed to the finger part of the human body, the device is mounted on the nail side of the finger, that is, on the back of the hand. And, the zeroth outer mounting part 4 is fixed to a portion ranging from the DIP joint to the terminal end portion, the first outer mounting part 5 is fixed to a portion intervening between the DIP and PIP joints, the second outer mounting part 6 is fixed to a portion intervening between the PIP and MP joints, and the third outer mounting part 7 is fixed to a palm part.

The respective outer mounting parts can be fixed to the respective portions of a finger constituting mounting targets using a flexible belt or the like.

By driving the drive shaft 8 in the mechanism longitudinal direction, the device can be applied as a device which supplies torque to the DIP, PIP and MP joints to support the natural gripping motions of the finger.

Figure 5:
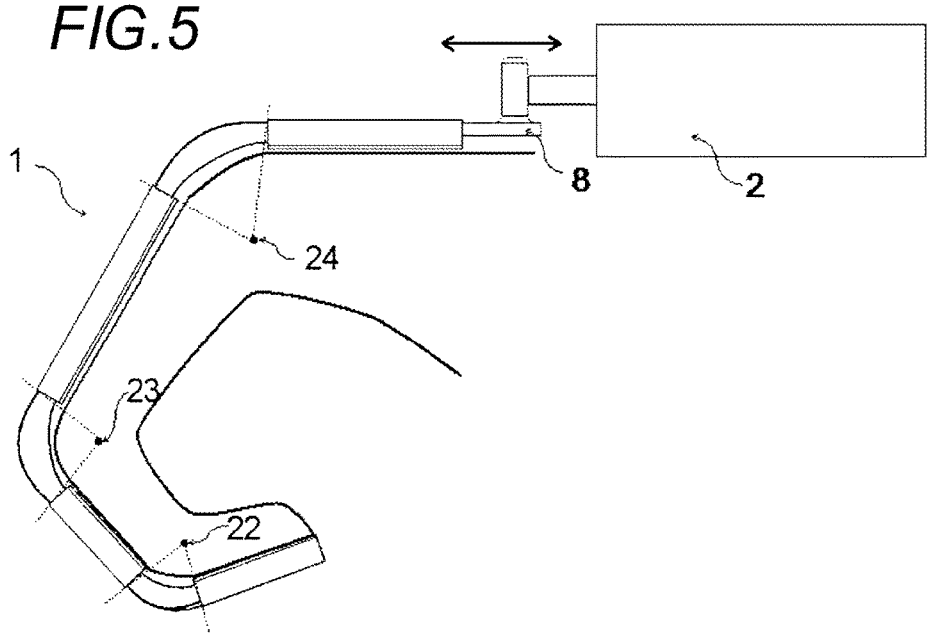
FIG. 5 is a diagram of the hand exoskeleton device using the three-layered sliding spring mechanism according to the embodiment of the present invention, when an actuator is mounted therein.

FIG. 5 shows an example of the three-layered connecting spring slide mechanism 1 when a direct acting actuator (an example of the drive mechanism 2) is mounted.

More specifically, when the drive shaft 8 is driven in a direction to approach the mechanism main body (in FIG. 5, in the left direction), the drive spring 15 slides in the same direction within the mechanism.

Since the outer mounting lower springs 12 to 14 have a fixed length and the outer mounting lower springs 12 to 14 and drive spring 15 are spaced from each other in the spring arrangement direction (in the vertical direction), the sliding movement of the drive spring 15 generates the flexing-direction movement of the drive spring 15.

As a result, as the spring lengths of the outer mounting upper springs 9 to 11 are extended by the slider mechanisms 16 to 18, the device is bent.

In this case, the outer mounting upper springs 9 to 11 prevent the excessive deformation and buckling of the drive spring 15.

Thus, the motion of the drive spring 15 in the mechanism longitudinal direction is changed to the rotation direction by the springs of the joints. That is, the motion of the drive spring 15 in the mechanism longitudinal direction causes the joints to operate in the flexing-direction.

Since the outer mounting upper springs 9 to 11, drive spring 15 and outer mounting lower springs 12 to 14 constituting three layers in the vertical direction are bent in a fan shape due to variations in the spring lengths caused by flexing, by setting the dimensions of the outer mounting parts 4 to 7 and springs 9 to 15 properly, the centers of rotation in the flexion movements of the joints can be made to coincide with the substantial centers of the motions 22 to 24 of the human finger joints on which the mechanism 1 is mounted. Here, the substantial centers of the motions 22 to 24 of the human finger joints, as shown in FIG. 5, exist outside the three-layered sliding spring mechanism 1.

The slider mechanisms 16 to 18 can simply realize the variable spring lengths by setting the partial portions of the spring as free ends and by allowing the free ends to slide freely in grooves formed within the outer mounting parts. Also, the one-side ends of the springs are formed in a T-like shape and cut-outs are formed in the outer mounting parts, thereby constituting stoppers.

The stoppers within the slider mechanisms 16 to 18 are prevented against the slide movements of a given amount or more and thus are prevented against the rotation movements. In this case, since the drive power is transmitted further to the joints on the terminal end side, thereby promoting the driving of the DIP and PIP joints existing on the terminal end side.

The sliding spring mechanism 1 can be structured such that the first, second and third outer mounting lower springs 12, 13 and 14 are constituted of a single continuous spring and are adhered to the respective outer mounting parts 4 to 7.

For the flexion and extension of the human finger, the lengths in the device longitudinal direction (mechanism longitudinal direction) of the springs of the three layers arranged in the upper portions of the joints are decided so that the device can be arranged according to the centers of the joints of the human finger.

In the device, the dimensions of the springs 9 to 15 and outer mounting parts 4 to 7 and the stiffness of the springs 9 to 15 provide indexes to change the timing for flexing the joints and, the motion of the device is adjustable by changing the indexes.

For example, the widths and thicknesses of the springs are determined by considering the material of the springs and balance between the joints. When the width and thickness of a certain joint are reduced, the joint is softened and is easy to bend first. Here, when the widths and thicknesses of the joints are set large as a whole, the rigidity of the whole device is high, thereby enabling the joints to generate higher torque. However, in this case, power necessary for driving increases. The stiffness of the springs therefore must be designed by considering the dimension of the human finger on which the device is mounted, the stiffness of the joints, support motions and the like.

In order to prevent the springs against breakage, preferably, the springs may be used within a range not reaching the yield stress of the spring materials.

In the drive mechanism of the embodiment of the present invention, there can be used a drive device connected to the drive shaft 8 and including an output shaft for outputting linear motion, for example, an actuator structured by combining a motor and a ball screw.

Here, in this structure, the distance in the mechanism vertical direction from the outer mounting upper springs 9 to 11 to the drive spring 15 can be set short. Thus, the distance between the drive spring 15 and the outer mounting lower springs 12 to 14 can be set long and, in the conversion of the motions of the joints to the rotation motions (flexion movements), rotation torque can be generated efficiently.

According to the above structure, using a structure similar to FIG. 1, by mounting the three-layered sliding spring mechanism 1 onto the human finger, power transmission for supporting the gripping motions of the finger is possible.

Also, according to this structure, since the drive spring is structured to freely slide in the longitudinal direction within the outer mounting parts 4 to 7, for example, when compared with the mechanism of Non-Patent Literature 7, the number of mechanisms parts can be reduced, thereby enabling reduction of size and weight as well as structure simplification.

While this device can be mounted on the human fingers except for thumbs, when it is constituted of two joints for simplified mounting, it can be also applied to the flexion and extension movement of thumbs.

Here, when a myoelectric sensor is mounted separately on the human body wearing this device and a sensor signal is input to the controller 3, support motions can be performed according to the myoelectric sensor signal.

Also, in the above-mentioned embodiment, the hand exoskeleton device compact, easy to carry and supporting the flexion and extension movements of fingers is constituted of the three-layered sliding spring mechanism. This device can be applied to the CPM (Continuous Passive Motion) training of fingers in which passive motions are executed repeatedly. Further, since this device is compact and light, it can provide a device structure capable of mounting on the human fingers and, for example, by operating the robot (this device) using the above-mentioned myoelectric sensor signal, the daily activity motions of a peripheral neuropathy patient can be supported.

According to the embodiment, there can be realized a device compact, light and capable of supporting the gripping motions of the human fingers. The device is characterized in that it can drive the flexion and extension of the three joints of the fingers using a single drive mechanism and it can transmit large drive power. Further, since the device body is flexible, it can be driven safely.

Although the present invention has been described heretofore with reference to the embodiment, the present invention is not limited to the embodiment but, of course, it also can be applied by changing it properly without departing from the subject matter thereof.

Although the present invention has been described heretofore specifically and with reference to the specific embodiment, of course, it is obvious to persons skilled in the art that various changes or modifications are also possible without departing from the spirit and scope of the present invention.

This application is based on Japanese Patent Application No. 2013-046449 filed on Mar. 8, 2013, the contents of which are incorporated herein by reference.

INDUSTRIAL APPLICABILITY

The hand exoskeleton device using the three-layered sliding spring mechanism of the present invention can apply, as a device for supporting daily activity motions, to a passive repetitive motion device or the like in rehabilitation.

REFERENCE SIGNS LIST

1: three-layered sliding spring mechanism
2: drive mechanism
3: controller
4: zeroth outer mounting part
5: first outer mounting part
6: second outer mounting part
7: third outer mounting part
8: drive shaft
9: first outer mounting upper spring
10: second outer mounting upper spring
11: third outer mounting upper spring
12: first outer mounting lower spring
13: second outer mounting lower spring
14: third outer mounting lower spring
15: drive spring
16: first slider mechanism
17: second slider mechanism
18: third slider mechanism
19: stopper within first slider mechanism
20: stopper within second slider mechanism
21: stopper within third slider mechanism
22: substantial center of motion of distal interphalangeal joint of human finger
23: substantial center of motion of proximal interphalangeal joint of human finger
24: substantial center of motion of metacarpophalangeal joint of human finger

The invention claimed is:

1. A hand exoskeleton device being a three-layered sliding spring mechanism drivable by a drive mechanism and mountable on a finger, the hand exoskeleton device comprising:

a zeroth outer mounting part, a first outer mounting part, a second outer mounting part and a third outer mounting part arranged in series along a longitudinal direction of the finger from a tip end of the hand exoskeleton device, wherein the zeroth outer mounting part and the first mounting part, the first outer mounting part and the second mounting part, and the second outer mounting part and the third outer mounting part are respectively connected to each other by multiple sets of upper springs and lower springs arranged in parallel in a vertical direction, the upper springs for fixing upper portions of the respective outer mounting parts are variable in length so that fixed ends of the upper springs are freely movable with sliding mechanisms by a specific distance in the finger longitudinal direction, the lower springs for fixing lower portions of the respective outer mounting parts are fixed at both ends to the respective outer mounting parts, the respective outer mounting parts include therein a drive spring capable of freely sliding only in the finger longitudinal direction, a tip end of the drive spring is fixed to the zeroth outer mounting part and the other end of the drive spring is fixed to a drive shaft, and the upper and lower springs connecting together the outer mounting parts and the drive spring constitute three layers in the vertical direction, wherein where the hand exoskeleton device is mounted onto a finger of a human body, the zeroth outer mounting part is fixed to a portion ranging from a distal interphalangeal joint to a terminal end of the finger, the first outer mounting part is fixed to a portion intervening between the distal interphalangeal joint and a proximal interphalangeal joint of the finger, the second outer mounting part is fixed to a portion intervening between the proximal interphalangeal joint and metacarpophalangeal joint of the finger, and the third outer mounting part is fixed to a palm part of the human body, and while the hand exoskeleton device is mounted on the human body, the drive shaft is driven on the finger of the human body in the longitudinal direction of the finger of the human body, thereby applying torque to the distal interphalangeal joint, the proximal interphalangeal joint and the metacarpophalangeal joint of the finger to support flexion and extension movements of the finger of the human body.

2. The hand exoskeleton device according to claim 1, wherein, in the three-layered sliding spring mechanism, lengths of the upper and lower springs respectively connecting together the zeroth outer mounting part, the first outer mounting part, the second outer mounting part and the third outer mounting part and a length of the drive spring serve as indexes for changing a timing for flexing the respective joints, and motions are adjustable by changing the spring length.

3. A hand exoskeleton device mountable on a finger, the device comprising:

a plurality of outer mounting parts arranged in series along a longitudinal direction of the finger;

a plurality of lower springs, each having a fixed length and connecting respective lower portions of the plurality of outer mounting parts;

a drive shaft driven in the longitudinal direction of the finger; and a drive spring passing through the plurality of outer mounting parts, and having one end fixed to an outer mounting part, a distance of which is the longest from the drive shaft among the plurality of outer mounting parts, and the other end fixed to the drive shaft, the drive spring being freely slidable along the longitudinal direction of the finger, wherein the lower springs and the drive spring are arranged in parallel to be separate from each other in vertical direction orthogonal to the longitudinal direction of the finger, and the drive shaft is driven to slidably move the drive spring, generate a flexing-direction movement of the drive spring and apply torque to joints of the finger.

4. The hand exoskeleton device according to claim 3, wherein the plurality of outer mounting members includes a zeroth outer mounting part, a first outer mounting part, a second outer mounting part and a third outer mounting part, the zeroth outer mounting part is fixed to a portion ranging from a distal interphalangeal joint to a terminal end of the finger, the first outer mounting part is fixed to a portion intervening between the distal interphalangeal joint and a proximal interphalangeal joint of the finger, the second outer mounting part is fixed to a portion intervening between the proximal interphalangeal joint and metacarpophalangeal joint of the finger, and the third outer mounting part is fixed to a palm part, and the drive shaft is driven in the longitudinal direction of the finger to apply torque to the distal interphalangeal joint, the proximal interphalangeal joint and the metacarpophalangeal joint of the finger.

5. The hand exoskeleton device according to claim 3, further comprising:

a plurality of upper springs, each having a variable length and connecting respective upper portions of the plurality of outer mounting parts, wherein the upper lower springs, the lower springs and the drive spring are arranged in parallel in the vertical direction and constitute a three layered sliding spring mechanism.

6. The hand exoskeleton device according to claim 5, wherein the lengths of the upper springs, the lengths of the lower springs and a length of the drive spring serve as indexes for changing a timing for flexing the respective joints of the finger, and a motion of the three layered sliding spring mechanism is adjustable by changing the lengths of the upper springs, the lengths of the lower springs and the length of the drive spring.

7. The hand exoskeleton device according to claim 5, wherein stiffness of the upper springs, stiffness of the lower springs and stiffness of the drive spring serve as indexes for changing a timing for flexing the respective joints of the finger, and a motion of the three layered sliding spring mechanism is adjustable by changing the stiffness of the upper springs, the stiffness of the lower springs and the stiffness of the drive spring.

* * * * *